US008221449B2

(12) United States Patent
Gadberry et al.

(10) Patent No.: US 8,221,449 B2
(45) Date of Patent: Jul. 17, 2012

(54) SURGICAL INSTRUMENT WITH REMOVABLE SHAFT APPARATUS AND METHOD

(75) Inventors: Donald L. Gadberry, San Juan Capistrano, CA (US); Ghassan Sakakine, Mission Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 906 days.

(21) Appl. No.: 11/345,964

(22) Filed: Feb. 2, 2006

(65) Prior Publication Data

US 2006/0129186 A1 Jun. 15, 2006

Related U.S. Application Data (62) Division of application No. 10/439,499, filed on May 15, 2003, now Pat. No. 7,025,775.

(51) Int. Cl.
A61B 17/00 (2006.01)

(52) U.S. Cl. .......................................... 606/205; 604/22

(58) Field of Classification Search .................. 606/174, 606/205–207, 170; 604/22–24; 403/92, 403/93, 96; 81/485, 487
See application file for complete search history.

(56) References Cited

U.S. PATENT DOCUMENTS

| | | | |
|---|---|---|---|
| 2,113,246 A | 4/1938 | Wappler | |
| 4,506,412 A * | 3/1985 | Hahn | 452/105 |
| 4,522,206 A * | 6/1985 | Whipple et al. | 606/174 |
| 4,896,986 A | 1/1990 | Terayama | |
| 5,211,050 A * | 5/1993 | Gouveia et al. | 72/409.16 |
| 5,238,002 A | 8/1993 | Devlin | |
| 5,254,130 A | 10/1993 | Poncet | |
| 5,282,800 A | 2/1994 | Foshee et al. | |
| 5,334,198 A | 8/1994 | Hart | |
| 5,342,391 A | 8/1994 | Foshee | |

(Continued)

FOREIGN PATENT DOCUMENTS

DE  28 52 559 A1  8/1980

(Continued)

OTHER PUBLICATIONS

Co-Pending U S. Appl. No. 10/976,505, filed Oct. 29, 2004 Title: Multiple-Angle Scissor Blade.

(Continued)

*Primary Examiner* — Victor Nguyen
(74) *Attorney, Agent, or Firm* — John F. Heal; Patrick Y. Ikehara; Pui Tong Ho (57) ABSTRACT

A surgical instrument includes a shaft having a proximal end and a distal end with an operating device disposed at the distal end. A cable assembly is carried by the shaft and extends proximally to a terminus. A handle assembly coupled to the cable assembly concludes a first handle and a second handle. The first handle includes portions configured to receive the terminus and the proximal end of the shaft while portions of the second handle are configured to receive the terminus of the cable assembly. The proximal end of the shaft and the terminus are simultaneously rotatable to cover the proximal end of the shaft to the portions of the first handle and to couple the terminus to the portions of the second handle. The handle assembly can be made sterilizable with a minimum of non-bearing surfaces, while the shaft assembly can be made disposable and interchangeable with various operating devices. An associated method includes the step of releasably locking the shaft assembly to the handle assembly.

22 Claims, 5 Drawing Sheets

U.S. PATENT DOCUMENTS

| | | | |
|---|---|---|---|
| 5,472,439 | A | 12/1995 | Hurd |
| 5,507,297 | A | 4/1996 | Slater |
| 5,562,699 | A | 10/1996 | Heimberger |
| 5,578,052 | A | 11/1996 | Koros |
| 5,618,303 | A | 4/1997 | Marlow |
| 5,618,304 | A | 4/1997 | Hart |
| 5,618,308 | A | 4/1997 | Holmes |
| 5,680,982 | A | 10/1997 | Schulze |
| 5,718,714 | A | 2/1998 | Livneh |
| 5,746,759 | A | 5/1998 | Meade |
| 5,782,748 | A | 7/1998 | Palmer |
| 5,792,165 | A | 8/1998 | Klieman |
| 5,928,255 | A | 7/1999 | Meade |
| 5,944,737 | A * | 8/1999 | Tsonton et al. ............... 606/205 |
| 6,036,706 | A | 3/2000 | Morejohn |
| 6,063,098 | A * | 5/2000 | Houser et al. ................ 606/169 |
| 6,077,290 | A | 6/2000 | Marini |
| 6,139,563 | A | 10/2000 | Cosgrove |
| 6,146,394 | A | 11/2000 | Morejohn |
| 6,358,267 | B1 * | 3/2002 | Murakami et al. ............ 606/205 |
| 6,443,944 | B1 | 9/2002 | Doshi |
| 7,025,775 | B2 * | 4/2006 | Gadberry et al. ............ 606/205 |
| 2001/0034536 | A1 | 10/2001 | Looper |
| 2002/0062136 | A1 | 5/2002 | Hillstead |
| 2002/0103498 | A1 | 8/2002 | Pagedas |
| 2002/0165564 | A1 | 11/2002 | Danitz |
| 2002/0198541 | A1 | 12/2002 | Smith |

FOREIGN PATENT DOCUMENTS

| | | |
|---|---|---|
| DE | 197 07 374 | 8/1998 |
| DE | 198 20 486 | 11/1998 |
| DE | 102 24 190 | 1/2004 |
| EP | 607594 A2 | 7/1994 |
| FR | 2 781 141 | 1/2000 |
| JP | 402057271 A | 2/1990 |
| WO | WO 02/26143 | 4/2002 |

OTHER PUBLICATIONS

Co-Pending U.S. Appl. No. 11/059,806, filed Feb. 17, 2005 Title: System and Method for Actuating a Laparoscopic Surgical Instrument.

Co-Pending U.S. Appl. No. 11/735,798, filed Apr. 16, 2007 Title: Laparoscopic Scissor Blades.

Co-Pending U.S. Appl. No. 11/334,027, filed Jan. 18, 2006 Title: Disposable Laparoscopic Instrument.

European Patent Office, Supplementary European Search Report for European Patent Application No. 04785513 5 based on International Application No. PCT/US04/13871 dated Apr. 22, 2008.

Allegiance Healthcare Corporation brochure entitled "V. Mueller's given a new twist to an old standby."

Allegiance Healthcare Corporation brochure entitled "One Good Turn Deserves Another".

* cited by examiner

SURGICAL INSTRUMENT WITH REMOVABLE SHAFT APPARATUS AND METHOD

CROSS-REFERENCE TO RELATED APPLICATIONS

This application is a divisional application of U.S. patent application Ser. No. 10/439,499, filed May 15, 2003 now U.S. Pat. No. 7,025,775, the disclosure of which is hereby incorporated by reference as if set in full herein.

BACKGROUND OF THE INVENTION

1. Field of the Invention

This invention relates generally to surgical instruments, and more specifically to instruments including an elongate shaft assembly facilitating access to distant operative sites.

2. Discussion of the Relevant Art

It is often desirable to cut tissue, occlude vessels or perform some other surgical procedure at a distant operative site. Under these circumstances, a surgical device having an elongate shaft assembly is typically required. Such a shaft assembly might have an operative device, such as a clamp or scissors, at its distal end, and a handle assembly at its proximal end for operating the device through the shaft assembly.

In the past, each instrument was formed as a single structure with its own handle assembly, shaft assembly, and associated operative device. Unfortunately, the complexity of the mechanics involved in these instruments has made it difficult to achieve adequate sterilization for reuse. In addition, the number of instruments which might be required for a particular procedure has often been significant. Where the shaft assembly was provided with a rigid configuration, these instruments tended to obstruct the surgical environment making it difficult for the surgeon to visualize or access the operative site.

More recently, flexible shaft assemblies have enabled the instrument to be bent away from the body opening, thereby facilitating the surgeon's access to the operative site. Even these instruments have continued to be manufactured as single structures however, and the problems relating to sterilization, access and overall cost have remained.

SUMMARY OF THE INVENTION

In accordance with the present invention, a surgical instrument is provided with an elongate shaft assembly that is removable from the handle assembly at a proximal end and may also be removable from the operative device at a distal end. The shaft assembly can be made from inexpensive, but non-sterilizable materials rendering the shaft assembly disposable. A coupling associated with the handle assembly is conceptually complex, but simple in its design, manufacture and use. This coupling assembly can be formed with large exposed surfaces and even a biasing spring held in position by point contacts and a minimum of bearing surfaces. This enables the handle assembly to be easily and repeatedly sterilized for use with each new disposable shaft assembly. The operative device at the distal end of the shaft assembly can be similarly provided with a coupling to render it disposable or reusable as desired.

With this system, an instrument including a handle assembly, shaft assembly and operative device can be assembled in the operating room as required for a particular procedure. With the versatility of the system, which can provide multiple operative capabilities with a single handle assembly and multiple disposable shaft assemblies, can greatly reduce the cost of a particular operative procedure. Sterilization is greatly facilitates by limiting the sterilized articles to those which are designed to minimize close tolerances and bearing surfaces. With coupling facilitating easy assembly, a locking relationship, and rigid support, alternative structures can be interchanged at both the proximal end and the distal end of the shaft assembly.

These and other features and advantages of the invention will become more apparent with a discussion of preferred embodiments and reference to the associated drawings.

DESCRIPTION OF THE DRAWINGS

FIG. 6b is a top plan view taken along lines 6b-6b of FIG. 6a;

FIG. 8b is a axial cross section view taken along lines 8b-8b of FIG. 8a;

DESCRIPTION OF PREFERRED EMBODIMENT AND BEST MODE OF THE INVENTION

Figure 1:
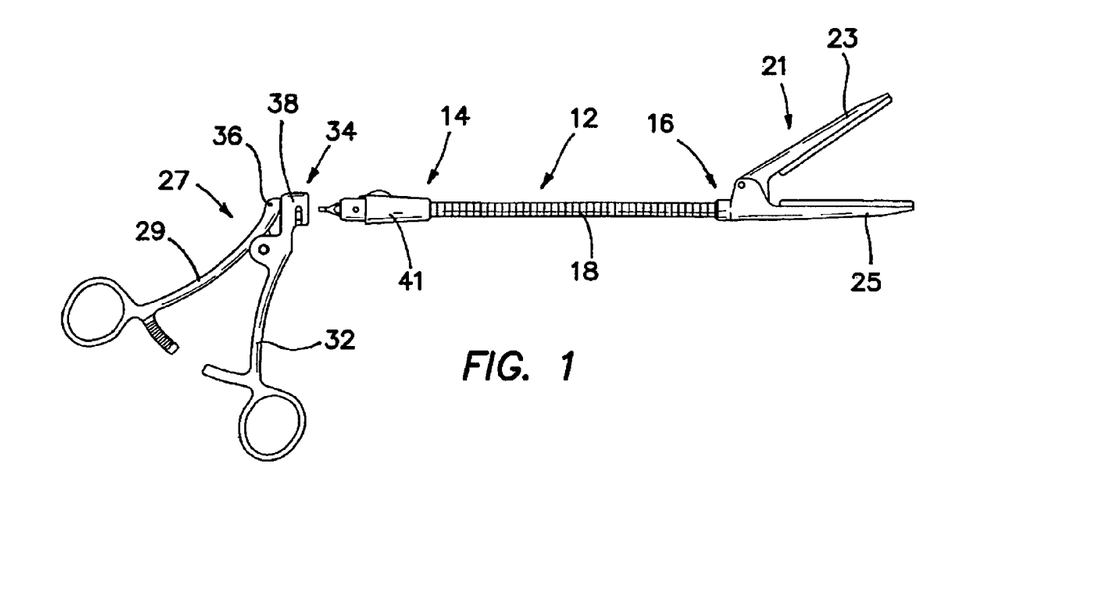
FIG. 1 is a side elevation view of one embodiment of the present invention, including a handle assembly, a shaft assembly, and an operative device.

A surgical clamp is illustrated in FIG. 1 and designated generally by the reference numeral 10. This clamp 10 is representative of any surgical instrument having any elongate shaft assembly 12 with a proximal end 14 and a distal end 16. The shaft assembly 12 will typically include a shaft 18 that is rigid or preferably flexible as illustrated in the embodiment of FIG. 1. At the distal end 16 of the shaft assembly 12, an operative device, such as a scissors or clamp 21 can be provided to perform a particular function at an operative site. The clamp 21 includes a pair of jaws 23 and 25, which are operable to receive and occlude a body conduit such as a blood vessel (not shown).

At the proximal end 14, the shaft assembly 12 is coupled to a handle assembly 27, which includes a proximal handle 29 and a distal handle 32. Of particular interest to the illustrated embodiment is a bayonet coupling 34 which permits removable attachment of the shaft assembly 12 to the handle assembly 27. It is the purpose of the handle assembly 27 to provide the user with an operating mechanism at the proximal end 14 which can function through the shaft assembly 12 to operate the clamp 21 at the distal end 16

Figure 2:
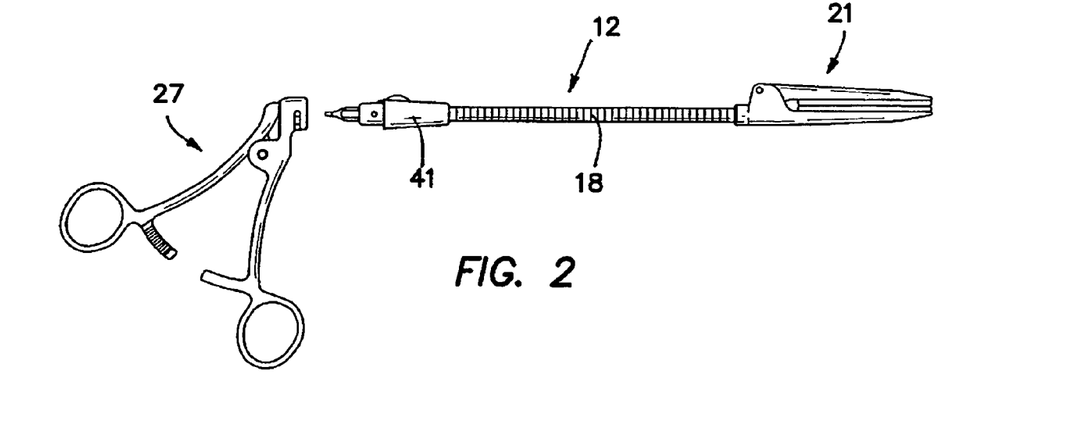
FIG. 2 is a side elevation view similar to FIG. 1, and illustrating the shaft assembly and the handle assembly in a separated relationship.

The bayonet coupling 34 includes portions 36 of the proximal handle 29, portions 38 of the distal handle 32, as well as a hub assembly 41 on the proximal end 14 of the shaft assembly 12. These elements are shown in the assembled view of FIG. 1 and also in the separated view of FIG. 2. With reference to FIG. 2, it can be seen that the surgical clamp 10 of this embodiment provides for separation of the shaft assembly 12 and associated clamp 21 from the handle assembly 27. This separation is of particular advantage when contemplating sterilization and reuse of the surgical clamp 10. With this separation, the handle assembly 27 can be sterilized and reused while the remainder of the surgical clamp can be made disposable. The different methods of handling these separate elements of the clamp 10 can be facilitated with the design and construction described below.

Figures 3, 4:
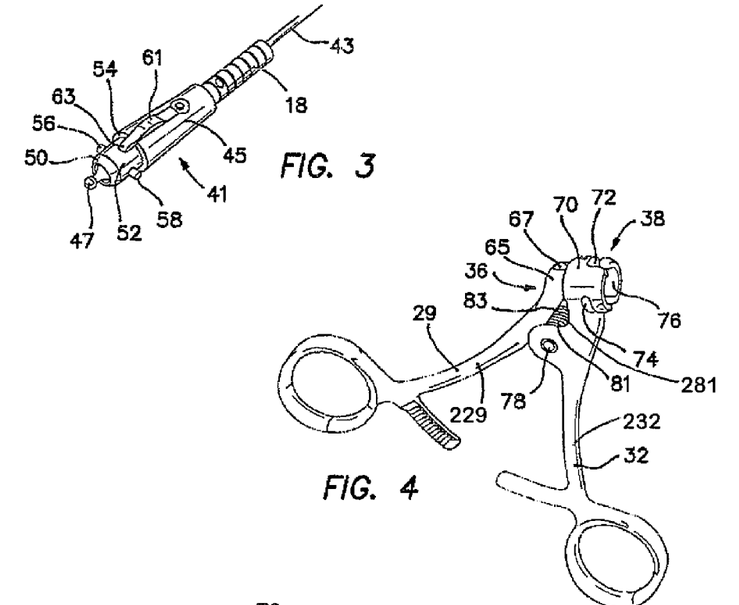
FIG. 3 is a perspective view of one embodiment of a coupling at the proximal end of the shaft assembly.
FIG. 4 is a perspective view of one embodiment of the handle assembly of the present invention.

In the perspective view of FIG. 3, the hub assembly 41 is illustrated at the proximal end 14 of the shaft assembly 12. In this view, it can be seen that the assembly 12 includes not only the hollow shaft 18, but also an actuating rod 43. The hub assembly 41 includes a housing 45 which is fixed to the proximal end of the shaft assembly 12. With the actuating rod 43 extending through the housing 45 and terminating at a pin or terminus 46. At the proximal end of the hub assembly 41, the housing 45 is defined by a tapered surface 50, and a cylindrical surface 52 which terminates at a shoulder 54. A pair of bayonet projections 56 and 58 extend radially outwardly from the cylindrical surface 52. Also illustrated in FIG. 3 is a locking lever 61 which is fixed to the housing 45 at its distal end. At its proximal end, a lug 63 is pivotal between positions radially inward and radially outward of the cylindrical surface 52.

Having described these elements of the hub assembly 41, it can now be seen how the shaft assembly 12 can be coupled to the handle assembly 27 which is illustrated in the perspective view of FIG. 4. In this view, it can be seen that the portions 36 of the proximal handle 29 function as a pin receiver 65 having a pin channel 67. In a similar manner, the portions 38 of the distal handle 32 function as a bayonet receiver 70 having projection channels 72 and 74 which are adapted to receive the bayonet projections 56 and 58 (FIG. 3), respectively. The bayonet receiver 70 also defines an axial channel 76 which is sized and configured to receive the cylindrical surface 52 of the hub housing 54.

Figure 5:
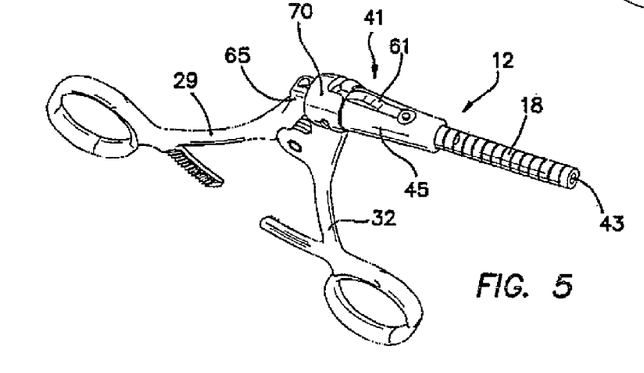
FIG. 5 is a perspective view of a coupling between the handle assembly and shaft assembly.

FIG. 4 further illustrates a pin 78 which pivotally attaches the proximal handle 29 to the distal handle 32. A spring 81 biases the handles 29 and 32 toward a proximate relationship as illustrated in FIG. 4. As illustrated in FIG. 4, a first outer surface 229 defines the proximal handle 29, a second outer surface 232 defines the distal handle 32, and a third outer surface 281 defines the spring 81. When the handle assembly 27 is coupled to the shaft assembly 12, as illustrated in FIG. 5, this proximate relationship between the handles 29 and 32 maintains the jaws 23 and 25 of the clamp 21 (FIG. 1) in an open relationship.

Figure 6:
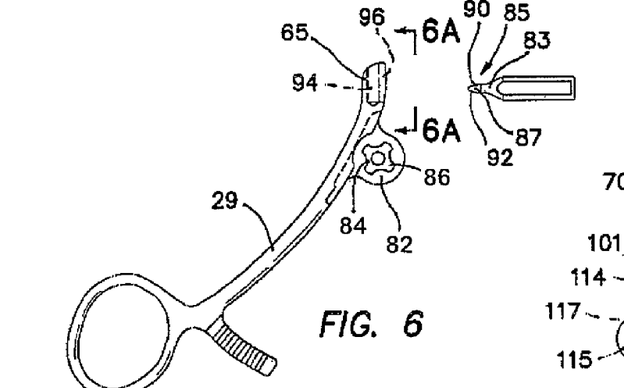
FIG. 6 is a side elevation view of a proximal handle associated with the handle assembly, and a complementary terminus associated with the shaft assembly.
Figures 9, 10:
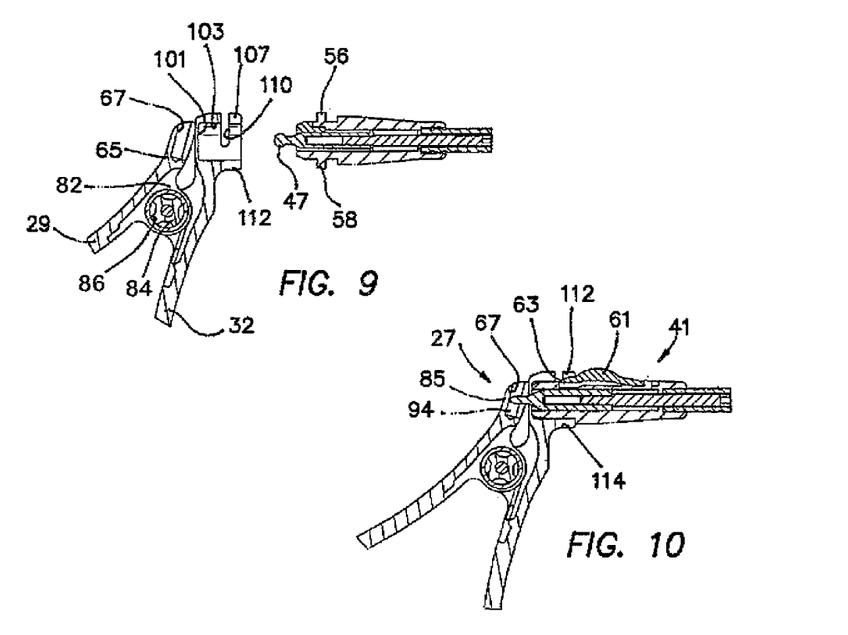
FIG. 9 is a cross section view showing a coupling portion at the distal end of the shaft assembly ready for insertion into a coupling portion associated with the handle assembly.
FIG. 10 is a cross section view illustrating the coupling portion of the shaft assembly in an operative, locked relationship with the coupling portion of the handle assembly.

The spring 81 and associated structure can be better understood with reference to FIG. 6 and the cross-section views of FIGS. 9 and 10. From these views it can be seen that the handle 29 can be formed with a flange 82 extending generally in the longitudinal direction of the instrument 10. A boss 84 can be provided to extend perpendicular to the flange 82 to provide an axial support for the spring 81 as illustrated in FIG. 9. The cross-sectional configuration of the boss 84 is of particular interest to this embodiment of the instrument 10. As best illustrated in FIG. 9, a plurality of supports 86 can be formed to extend radially outwardly toward the spring 81. These supports 86 provide point contact with the spring 81 while maintaining the spring generally coaxially with the boss 84. The point contacts are desirable to minimize the area of interference between the spring 81 and the boss 84, thereby greatly facilitating the exposure of surfaces for sterilization.

In FIG. 6, the terminus 47 associated with the hub assembly 41 is illustrated in a spaced relationship with the associated proximal handle 29. From this view it can be seen that the terminus 47 is defined by a conical surface 83 which is tapered proximally inwardly to an enlargement 85. The enlargement 85 is defined by a spherical surface 87 having a particular diameter, and a pair of opposing surfaces 90 and 92 which are spaced by a distance less than the particular diameter. In the illustrated embodiment, these surfaces 90 and 92 converge slightly in the proximal direction.

Figure 6A:
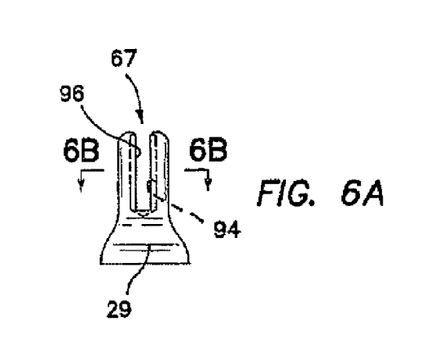
FIG. 6a is a side elevation view taken along lines 6a-6a of FIG. 6.

As shown in FIG. 6a, the receiver 65 associated with the handle 29 is sized and configured to receive the enlargement 85 associated with the terminus 47. To that end, the terminus channel 67 is formed with a keyhole cross section best illustrated in FIG. 6b. This cross section includes an enlarged circular channel 94 and a smaller lead channel 96. In operation, the enlarged channel 94 must have a diameter greater than that of the spherical surface 87 associated with the terminus 47. The lead channel 96 must be smaller than this diameter but larger than the distance separating the opposing surfaces 90 and 92.

Figure 6B:
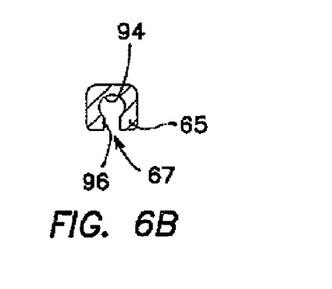

In operation, the terminus 47 is inserted into the lead channel 96 with the opposing surfaces 90 and 92 oriented to pass through the lead channel 96. Once the enlargement 85 has cleared the lead channel 96, it can be rotated an angular distance such as ninety degrees, so that the surfaces 90 and 92 are positioned transverse to the lead channel 96. With this orientation, the enlargement 85 is held within the enlarged channel 94 and locked in place by the narrower lead channel 96.

Figure 7:
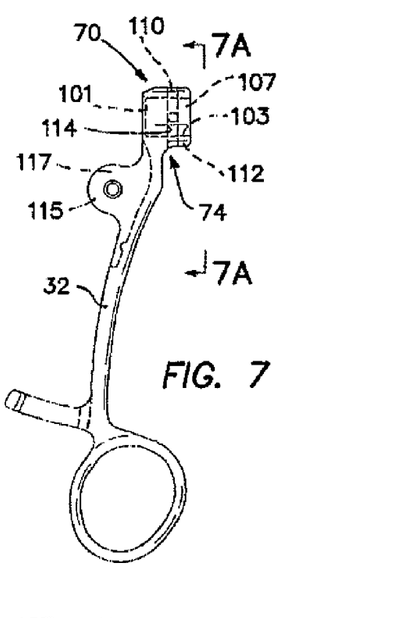
FIG. 7 is a side elevation view of a distal handle associated with the handle assembly.
Figure 7A:
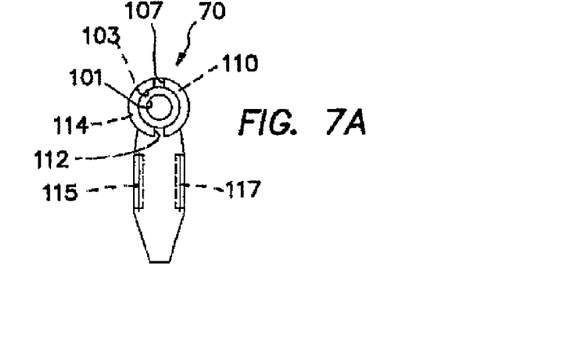
FIG. 7a is a side elevation view taken along line 7a-7a of FIG. 7.

The distal handle 32 is illustrated in FIG. 7 and shows in greater deal the channels associated with the bayonet receiver 70. From this view, and that of FIG. 7a, it can be seen that the bayonet receiver 70 in this embodiment has a cylindrical configuration and includes a through-channel 101 which extends entirely through the receiver 70, and a larger lead channel 103 which terminates at a shoulder 105. The through-channel 101 in a preferred embodiment is large enough to receive the terminus 47 (FIG. 3) associated with the hub 41, while the lead channel 103 is configured to receive the cylindrical surface 52 (FIG. 3) of the hub 41.

The projection channels 72 and 74 are sized in this configuration to receive the bayonet projections 56 and 58 discussed with reference to FIG. 3. The projection channel 72 includes an axial lead passage 107 which communicates with a radial locking passage 110. Similarly, the projection channel 74 includes an axial lead passage 112 and a radial locking passage 114. As noted in greater detail below, these projection channels 72 and 74 are configured to receive the projections 56 and 58 in the respective lead passages 107 and 112 and ultimately the respective locking passages 110 and 114.

The distal handle 30 in the illustrated embodiment also includes a pair of opposing flanges 115 and 117 which are similar to the flange 82 associated with the proximal handle 29. These flanges 115, 117, can be appropriately drilled to receive the pivot pin 78 in the only bearing relationship associated with the handle assembly 27. As the proximal handle 29 is joined to the distal handle 32, the pin 78 is progressively inserted through the flange 117, the flange 82, the boss 84 and spring 81, and the flange 115.

Figures 8, 8A:
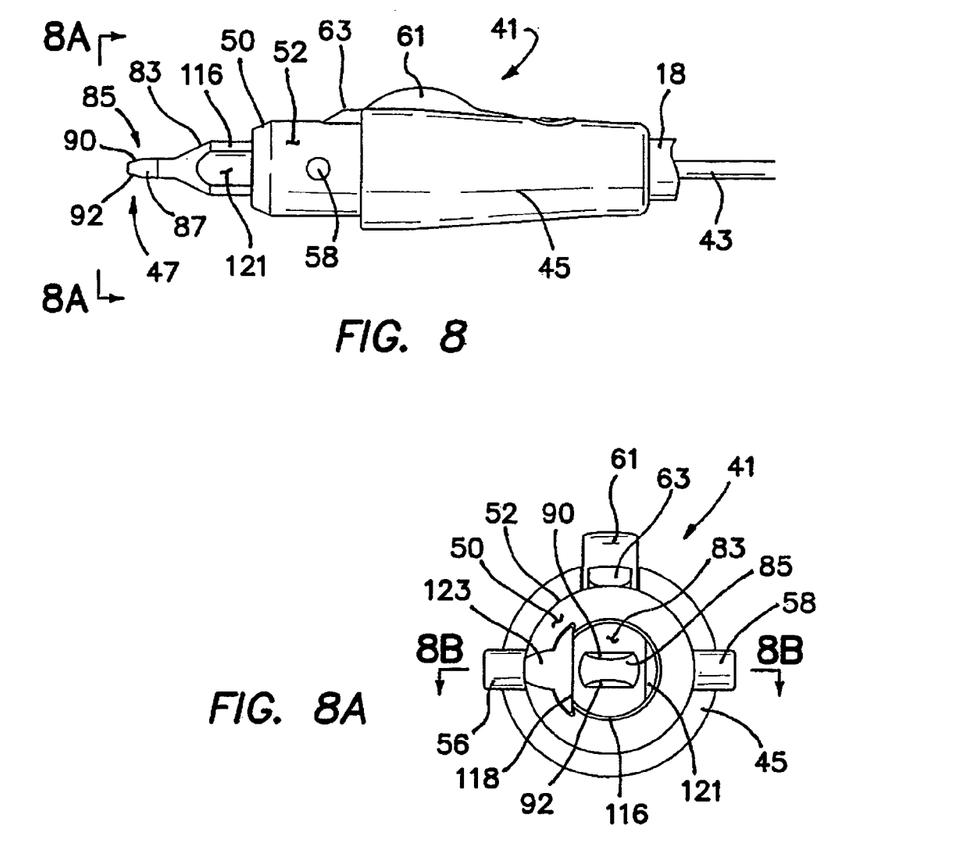
FIG. 8 is a side elevation view of one embodiment of the coupling disposed at the proximal end of the shaft assembly.
FIG. 8a is a front elevation view taken along lines 8a-8a of FIG. 8.

The construction of the hub assembly 41 is of particular importance to the present invention. This assembly is shown in greater detail in the illustrations of FIGS. 8 and 8a. In these views, many of the elements previously discussed with reference to FIG. 3 are also apparent. Thus the shaft 18 and actuating rod 43 can be seen in combination with the hub assembly 41, including the housing 45 leading distally to the cylindrical-surface 53 and associated projections 56 and 58. In this view it can also be seen that the terminus 47 includes the enlargement 85 and outer surfaces including the conical surface 83 and a cylindrical surface 116. A pair of opposing planar surfaces 118 and 121 can be cut into this cylindrical surface 116 to facilitate orientation of the terminus 47 relates to the housing 45 with a key 123. In this preferred embodiment, the opposing surfaces 90 and 92 of the enlargement 85 are aligned with the bayonet projections 56 and 58 as best illustrated in FIG. 8a.

Figure 8B:
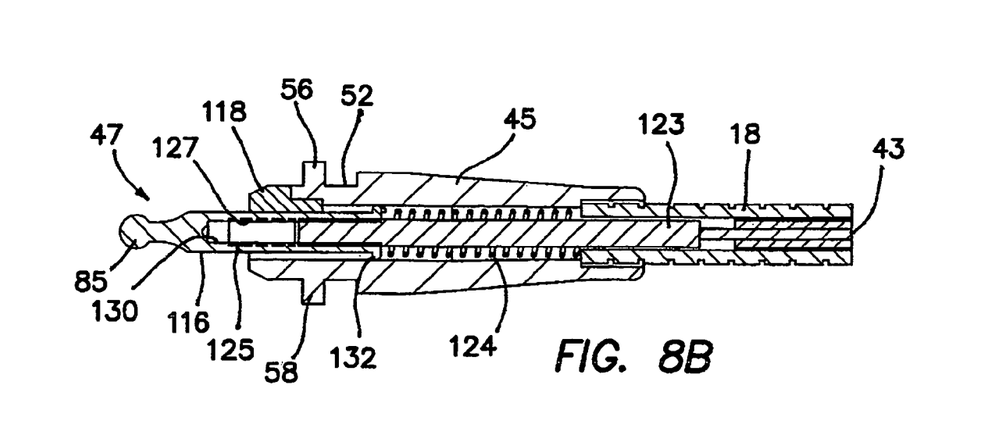

Interior elements of the hub assembly 41 are illustrated in the axial cross section view of FIG. 8b. In this view it can be seen that the actuating rod 43 carried by the shaft 18 terminates proximally in a cylinder 123 having external threads 125. These threads 125 are intended to mate with internal threads 127 which define a cylindrical cavity 130 in the distal end of the terminus 47. A shoulder flange 132 at the distal end of the terminus 47 is biased proximally by compression spring 124. This spring 124 tends to bias the terminus 47 and the actuating rod 43 proximally, along with the actuating rod 43 to hold the jaws 23 and 25 of the clamp 21 in a normally closed position as illustrated in FIG. 1.

Having discussed in detail the handle 29 assembly, the handles 29 and 32, and the hub assembly 41, it can now be better appreciated how the shaft assembly 12 can be attached to the handle assembly 27. This process is illustrated in the cross sectional views of FIGS. 9 and 10. Initially, the hub assembly 41 is oriented with the bayonet projections 56 and 58 aligned with the lead passages 107 and 112, respectively of the receiver 70. As the hub assembly 41 is moved proximally into the handle assembly 27, the terminus 47 passes through the lead channel 103 and the through-channel 101 into the pin channel 67 of the receiver 65. Similarly, the cylindrical surface 52 of the hub assembly 41 passes into the lead channel 103.

When the hub assembly 41 is seated in the lead channel 103 and the terminus 47 is seated in the pin channel 67, the projections 56 and 58 will have passed through the lead channels 107 and 112 respectively, into alignment with the lock passage 110 and 114, respectively. At this point, the hub assembly 41 and shaft assembly 12 can be rotated axially, 90° for example, to the position illustrated in FIG. 10. In this rotating process the projections 56 and 58 will travel along the respective locking passages 110 and 114. At the same time, the terminus 47 will turn to lock the enlargement 85 in the enlarged channel 94 of the pin receiver 65. When the projections 56 and 58 reach the closed ends of the passages 110 and 114, respectively, the housing 45 is fixed in the bayonet receiver 70 of the handle 32. Similarly, the terminus 47 is fixed within the pin receiver 65 of the handle 29.

The handle assembly 27 and shaft assembly 12 can be locked in this operative position by the locking lever 61. The lug 63 associated with this lever 61 is depressed during the insertion step and rotating step by the structure defining the lead channel 103 of the bayonet receiver 70. This depression of the lug 63 and associated locking lever 61 continues until the lug 63 reaches the lead passage 112 associated with the bayonet receiver 70. Within this lead passage 112, the lug 63 is free to rise to an elevated position, thereby locking the hub assembly 41 in the operative position relative to the handle assembly 27, as illustrated in FIG. 10.

Having attached the shaft assembly 12 to the handle assembly 27, the surgical clamp 10 is ready for use. Typically the surgeon will bend the flexible shaft 18 to a configuration facilitating passage of the clamp 21 through a torturous path to a distant operative site. At this site, the scissor handles 29 and 32 can be separated, thereby moving the pin receiver 65 toward the bayonet receiver 70. This also functions to push the actuating rod 43 distally within the shaft 18, thereby causing the jaws 23 and 25 of the clamp 21 to open.

With the jaws 23 and 25 open, a body conduit (not shown) at the operative site can be engaged and occluded by closing the jaws 23 and 25 on the conduit. Closing the jaws 23 and 25 is achieved in the reverse manner by squeezing the handles 29 and 32 of the handle assembly 27. This functions to pull the actuating rod proximally within the shaft 18, thereby causing the jaws 23 and 25 to move to the desired closed position.

Once the body conduit, such as the blood vessel, has been engaged by the clamp 21 at the operative site, the handle assembly 27 can be released to free the surgeon's hands for other steps in the operative procedure. One of these steps may include pending the shaft 18 so that the handle assembly 27 is moved away from the operative environment to facilitate access with other surgical instruments.

Figure 11:
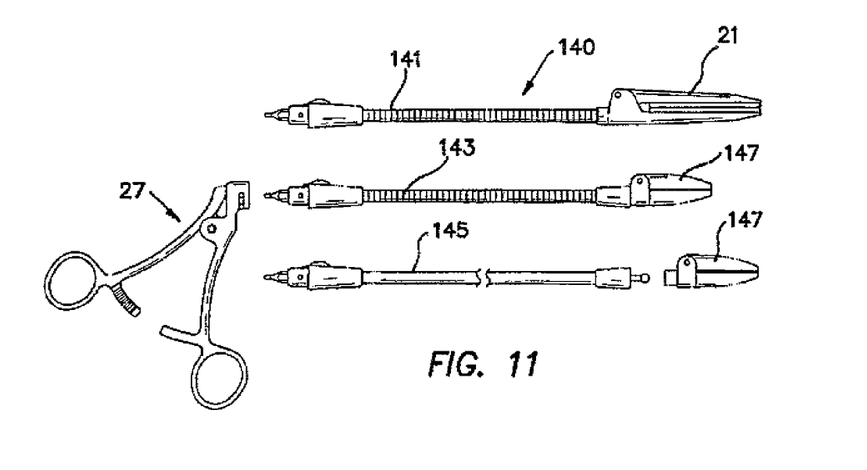
FIG. 11 is a side elevation view of a kit including a single handle assembly and multiple shaft assemblies and operative devices.

From the foregoing discussion, it can be seen that the instrument 10 of the present invention lends itself to the configuration of a highly versatile kit such as that designated by the reference numeral 140 in FIG. 11. This kit 140 might include, for example, a single handle assembly 27, multiple shaft assemblies such as those designated by the reference numerals 141, 143, and 145, and multiple operating devices, such as the clamp 21 and scissors 147. The shaft assemblies 141, 143 and 145 can offer a variety of lengths and flexibility in the kit 140. The various operative devices such as the clamp 21 and scissors 147, can either be formed integral with a shaft assembly, or made detachable as illustrated for the shaft assembly 145.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

The invention claimed is:

1. A surgical instrument, comprising:
a shaft assembly having a proximal end and a distal end and being operable to perform a surgical function at the distal end;
a handle assembly coupled to the proximal end of the shaft assembly and being moveable to operate the shaft assembly;

a first outer surface defining a proximal handle of the handle assembly;

a second outer surface defining a distal handle of the handle assembly, the distal handle having a pivotal relationship with the proximal handle;

a third outer surface defining a spring disposed between the proximal handle and the distal handle of the handle assembly; the spring biasing the handles to an operating state;

a boss carried by one of the proximal handle and the distal handle the boss maintained generally coaxially with the spring, and the boss comprising a plurality of supports axially supporting the spring in a non-bearing relationship with the spring;

a pin engaging the proximal handle and the distal handle along particular surfaces which comprises the only bearing surfaces of the handle assembly; and the first, second, and third surfaces of the handle assembly, except for the particular surfaces, being substantially exposed in order to facilitate sterilization; wherein the shaft assembly defines a longitudinal axis of the surgical instrument, wherein the surgical instrument further comprises a flange extending generally longitudinally with respect to one of the proximal handle and the distal handle and wherein the boss extends from the flange generally perpendicularly to the flange.

2. The surgical instrument recited in claim 1, wherein the plurality of supports extend radially outwardly of the boss to support the spring with substantially point contact to facilitate sterilization of the instrument.

3. The surgical instrument recited in claim 2, wherein the supports contact the spring along non-bearing surfaces.

4. The surgical instrument recited in claim 3, wherein surfaces of the supports provide substantially point contact with the spring.

5. The surgical instrument recited in claim 1, further comprising:

a coupling releasably attaching the shaft assembly to the handle assembly.

6. The surgical instrument recited in claim 5, further comprising:

a locking lever included in the coupling and being operable to facilitate release of the shaft assembly from the housing assembly.

7. The surgical instrument recited in claim 5, wherein the coupling comprises a bayonet coupling.

8. The surgical instrument recited in claim 1, wherein the shaft assembly includes a flexible shaft.

9. The surgical instrument of claim 1, wherein the shaft assembly further comprises an operative device disposed at the distal end of the shaft assembly, the operative device operable to perform the surgical function.

10. The surgical instrument of claim 9, wherein the shaft assembly further comprises a coupling such that the operative device is detachable from the shaft assembly.

11. The surgical instrument of claim 9, wherein the operative device comprises one of a clamp and scissors.

12. The surgical instrument of claim 1, wherein the proximal handle comprises a flange having the boss extending therefrom, and wherein the distal handle comprises two flanges.

13. The surgical instrument of claim 12, wherein the pin extends through the flange, the boss of the proximal handle, and the two flanges of the distal handle.

14. A surgical instrument, comprising:

a disposable shaft assembly having a proximal end and a distal end and being operable to perform a surgical function at the distal end;

a reusable handle assembly removably couplable to the proximal end of the shaft assembly and being moveable to operate the shaft assembly, the handle assembly comprising;

a proximal handle having a first outer surface;

a distal handle having a second outer surface, the distal handle pivotably coupled to the proximal handle, the pivotal coupling of the proximal handle to the distal handle defining particular surfaces which comprise the only bearing surfaces of the handle assembly;

a spring disposed between the proximal handle and the distal handle of the handle assembly, the spring having a third outer surface, and the spring biasing the handles to an operating state; and a boss carried by one of the proximal handle and the distal handle the boss maintained generally coaxially with the spring, and the boss comprising a plurality of supports axially supporting the spring in a non-bearing relationship with the spring; and wherein the first, second, and third surfaces of the handle assembly, except for the particular surfaces, are substantially exposed for sterilization; wherein the plurality of supports extend radially outwardly of the boss to support the spring with substantially point contact to facilitate sterilization of the instrument.

15. The surgical instrument recited in claim 14, wherein the supports contact the spring along non-bearing surfaces.

16. The surgical instrument recited in claim 15, wherein surfaces of the supports provide substantially point contact with the spring.

17. The surgical instrument recited in claim 14, further comprising:

a coupling releasably attaching the shaft assembly to the handle assembly.

18. The surgical instrument recited in claim 17, further comprising:

a locking lever included in the coupling and being operable to facilitate release of the shaft assembly from the housing assembly.

19. The surgical instrument recited in claim 14, wherein the shaft assembly comprises:

a hub assembly at the proximal end of the shaft assembly, the hub assembly adapted to couple to the handle assembly;

a hollow shaft extending from the proximal end of the shaft assembly to the distal end of the shaft assembly;

an actuating rod slidable within the hollow shaft; and an operative device at the distal end of the shaft assembly.

20. The surgical instrument recited in claim 19, wherein the operative device is detachable from the shaft assembly.

21. A surgical kit comprising:

a reusable handle assembly comprising;

a proximal handle having a first outer surface;

a distal handle having a second outer surface, the distal handle pivotably coupled to the proximal handle, the pivotal coupling of the proximal handle to the distal handle defining particular surfaces which comprise the only bearing surfaces of the handle assembly;

a spring disposed between the proximal handle and the distal handle of the handle assembly, the spring having a third outer surface, and the spring biasing the handles to an operating state; and a boss carried by one of the proximal handle and the distal handle the boss maintained generally coaxially with the spring, and the boss comprising a plurality of supports axially supporting the spring in a non-bearing relationship with the spring; and wherein the first, second, and third surfaces of the handle assembly, except for the particular surfaces, are substantially exposed for sterilization; and a plurality of disposable shaft assemblies each having a proximal end and a distal end and being operable to perform a surgical function at the distal end; and wherein the handle assembly is removably couplable to the proximal end of each of the shaft assemblies and is moveable to operate each of the shaft assemblies; wherein the plurality of disposable shaft assemblies comprises a first shaft assembly including a clamp and a second shaft assembly including scissors.

22. The surgical kit of claim 21, wherein each of the shaft assemblies of the plurality of shaft assemblies has a length from the proximal end to the distal end, and wherein at least one of the shaft assemblies has a different length than another of the shaft assemblies.

* * * * *